US007246615B2

(12) United States Patent
Bartels et al.

(10) Patent No.: US 7,246,615 B2
(45) Date of Patent: Jul. 24, 2007

(54) ATOMISING NOZZLE AND FILTER AND SPRAY GENERATING DEVICE

(75) Inventors: Frank Bartels, Hattingen (DE); Wulf Bachtler, Mainz (DE); Stephen T Dunne, Suffolk (GB); Joachim Eicher, Dortmund (DE); Bernhard Freund, Gau-Algesheim (DE); William B Hart, Ipswich (GB); Christoph Lessmoellmann, Gernsbach (DE)

(73) Assignee: Boehringer International GmbH, Rhein (DE)

( * ) Notice: Subject to any disclaimer, the term of this patent is extended or adjusted under 35 U.S.C. 154(b) by 975 days.

(21) Appl. No.: 10/291,624

(22) Filed: Nov. 12, 2002

(65) Prior Publication Data

US 2003/0075623 A1 Apr. 24, 2003

Related U.S. Application Data

(63) Continuation of application No. 09/472,169, filed on Dec. 27, 1999, now Pat. No. 6,503,362, which is a continuation of application No. 09/303,670, filed on May 3, 1999, now Pat. No. 6,007,676, which is a continuation of application No. 08/661,741, filed on Jun. 11, 1996, now Pat. No. 5,911,851, which is a continuation of application No. 08/128,021, filed on Sep. 29, 1993, now Pat. No. 5,472,143.

(30) Foreign Application Priority Data

| Sep. 29, 1992 | (GB) | ................................... 9220505.3 |
| Oct. 24, 1992 | (GB) | ................................... 4236037.4 |
| Jul. 19, 1993 | (GB) | ................................... 9314804.7 |

(51) Int. Cl.
| A61M 11/00 | (2006.01) |
| B05B 1/26 | (2006.01) |
| B05D 1/02 | (2006.01) |
| G03F 7/00 | (2006.01) |

(52) U.S. Cl. ........................... 128/200.22; 128/200.21; 128/200.23; 239/462; 239/543; 239/544; 239/553

(58) Field of Classification Search ........... 128/200.14, 128/200.21, 200.22, 203.13, 200.23; 239/462, 239/543, 544, 590–590.5, 553–553.5
See application file for complete search history.

(56) References Cited

U.S. PATENT DOCUMENTS 3,347,473 A 10/1967 Steck
(Continued)

FOREIGN PATENT DOCUMENTS

DE 916 879 8/1954
(Continued)

OTHER PUBLICATIONS

Patent Abstracts of Japan, vol. 005, No. 183, Nov. 21, 1981.
(Continued)

*Primary Examiner*—Justine R. Yu
*Assistant Examiner*—K C Matter
(74) *Attorney, Agent, or Firm*—Sterne, Kessler, Goldstein & Fox P.L.L.C.

(57) ABSTRACT

A nozzle assembly for use in atomizing and generating sprays from a fluid. The nozzle assembly includes two members, each with generally planar surfaces, that are joined together. A first set of channels is formed in the generally planar surface of a first one of the members to form, in cooperation with the generally planar surface of the second of the members, a plurality of filter passageways. A plenum chamber is formed in the first member. The plenum chamber is in fluid communication with and downstream of the plurality of filter passageways. A second set of channels is formed in the generally planar surface of the first member to form, in cooperation with the generally planar surface of the second member, a plurality of nozzle outlet passageways. These nozzle outlet passageways are in fluid communication with the plenum chamber. The nozzle outlet passageways include a plurality of nozzle outlets which are adapted to discharge a plurality of fluid jets that impinge on one another to thereby atomize a flow of fluid.

20 Claims, 9 Drawing Sheets

U.S. PATENT DOCUMENTS

Figure 1:
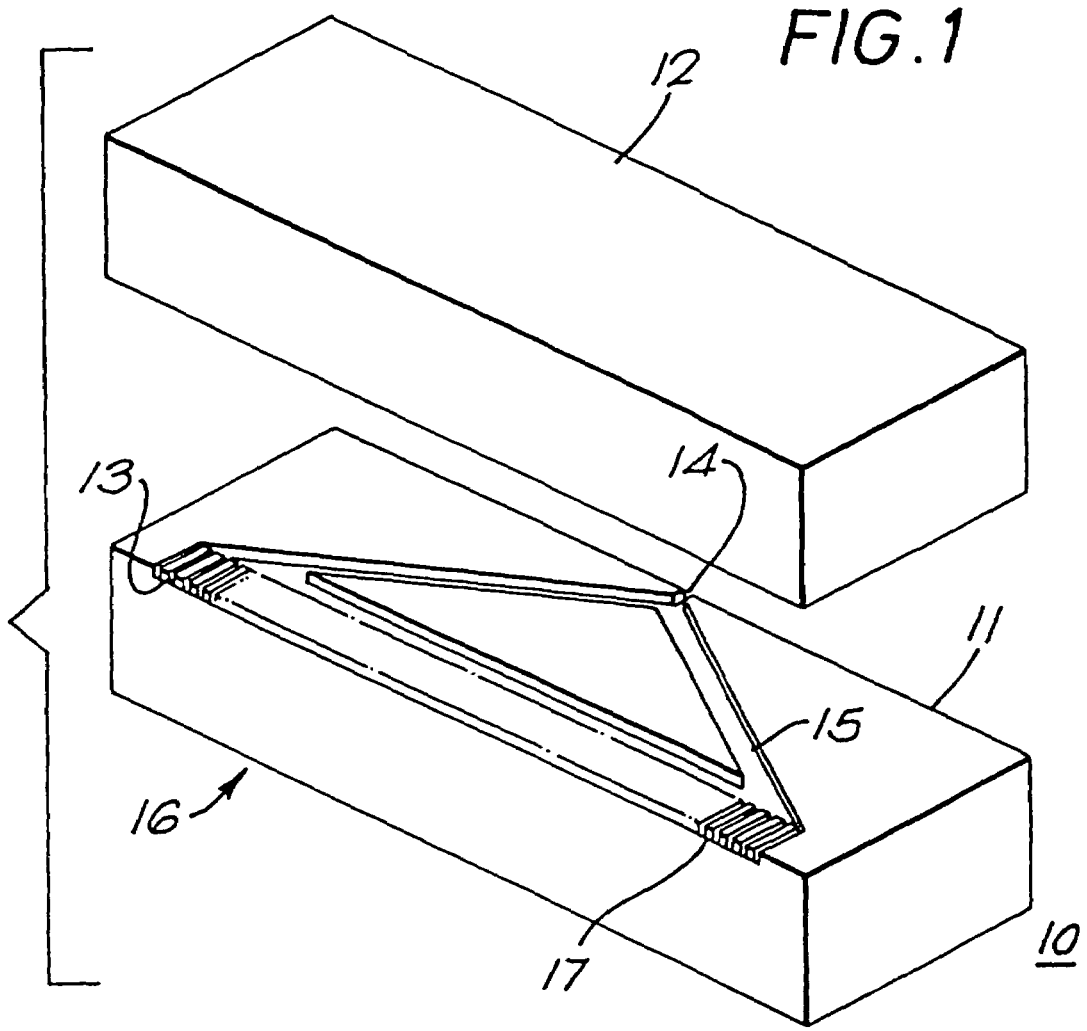
Figure 1A:
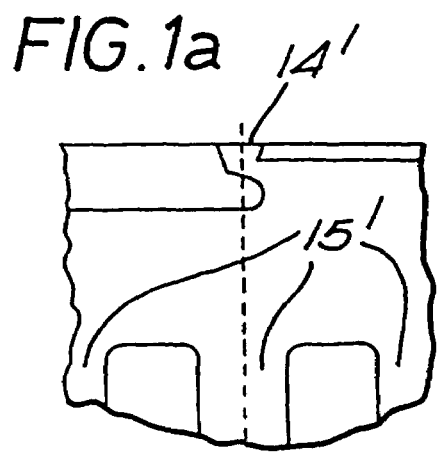

| | | | |
|---|---|---|---|
| 3,397,278 A | 8/1968 | Pomerantz | |
| 3,615,054 A | 10/1971 | La Botz | |
| 3,647,143 A * | 3/1972 | Gauthier et al. | 239/342 |
| 3,771,724 A | 11/1973 | Rose et al. | |
| 3,921,916 A | 11/1975 | Bassous | |
| 4,151,955 A | 5/1979 | Stouffer | |
| 4,601,921 A | 7/1986 | Lee | |
| 4,681,258 A | 7/1987 | Jenkins et al. | |
| 4,688,056 A | 8/1987 | Noguchi et al. | |
| 4,828,184 A | 5/1989 | Gardner et al. | |
| 4,829,324 A | 5/1989 | Drake et al. | |
| 4,875,968 A | 10/1989 | O'Neill et al. | |
| 4,899,937 A | 2/1990 | Haruch | |
| 4,915,718 A | 4/1990 | Desai | |
| 5,056,511 A * | 10/1991 | Ronge | 128/200.14 |
| 5,160,403 A | 11/1992 | Fisher et al. | |
| 5,332,466 A | 7/1994 | Nozawa | |
| 5,334,247 A | 8/1994 | Columbus et al. | |
| 5,472,143 A * | 12/1995 | Bartels et al. | 239/462 |
| 5,487,378 A | 1/1996 | Robertson et al. | |
| 5,587,128 A | 12/1996 | Wilding et al. | |
| 5,770,076 A | 6/1998 | Chu et al. | |
| 5,855,801 A | 1/1999 | Lin et al. | |
| 5,911,851 A | 6/1999 | Bartels et al. | |
| 6,007,676 A | 12/1999 | Bartels et al. | |

FOREIGN PATENT DOCUMENTS

| | | |
|---|---|---|
| EP | 0041729 | 12/1981 |
| EP | 0231432 A2 | 8/1987 |
| EP | 0231432 A3 | 8/1987 |
| EP | 0397441 | 11/1990 |
| EP | 02552208 B1 | 3/1992 |
| GB | 1515892 | 6/1978 |
| GB | 2065505 | 7/1981 |
| JP | 50-29165 | 9/1975 |
| JP | 50-29166 | 9/1975 |
| JP | 53-007819 | 1/1978 |
| JP | 56-113367 | 9/1981 |
| JP | 57-182452 | 11/1982 |
| JP | 2-229050 | 9/1990 |
| JP | 3-267173 | 11/1991 |
| WO | WO 79/00236 | 5/1979 |
| WO | WO 91/14468 | 10/1991 |
| WO | WO 92/10301 | 6/1992 |
| WO | WO 92/10306 | 6/1992 |
| WO | WO 92/19383 | 11/1992 |
| WO | WO 93/11862 | 6/1993 |
| WO | WO 97/29283 | 8/1997 |

OTHER PUBLICATIONS

Patent Abstracts of Japan, vol. 005, No. 194, Dec. 10, 1981.

Patent Abstracts of Japan, vol. 007, No. 029, Feb. 5, 1983.

Angell, J. et al., "Silicon Micromechanical Devices", *Scientific American*, Apr. 1983, pp. 36-47.

Peterson. K., "Silicon as a Mechanical Material", *Proceedings of the IEEE*, vol. 70, No. 5, May 1982, pp. 420-456.

* cited by examiner

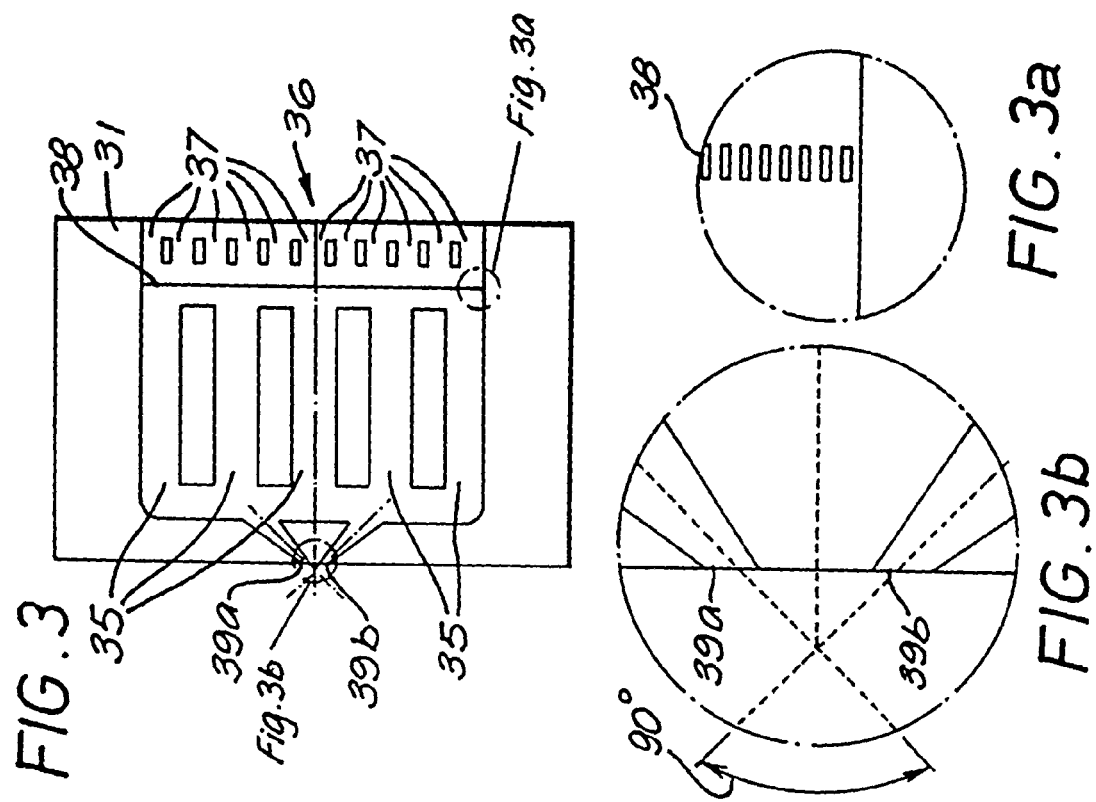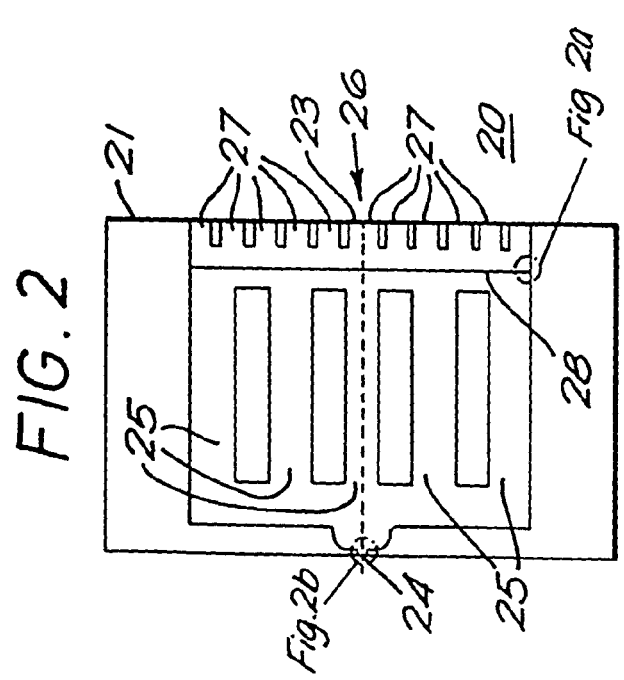

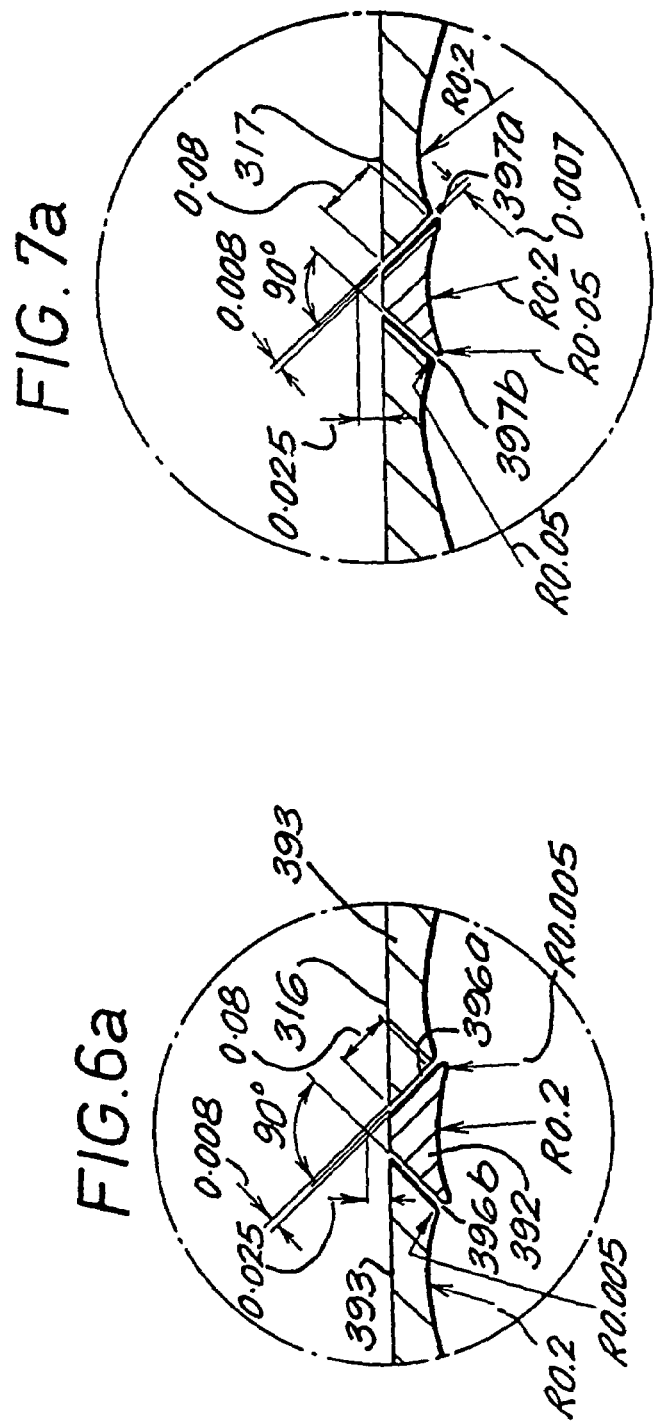

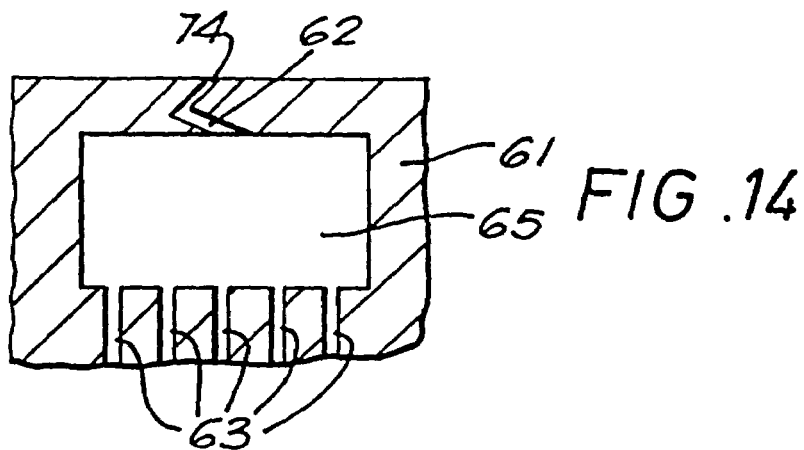
FIG. 14
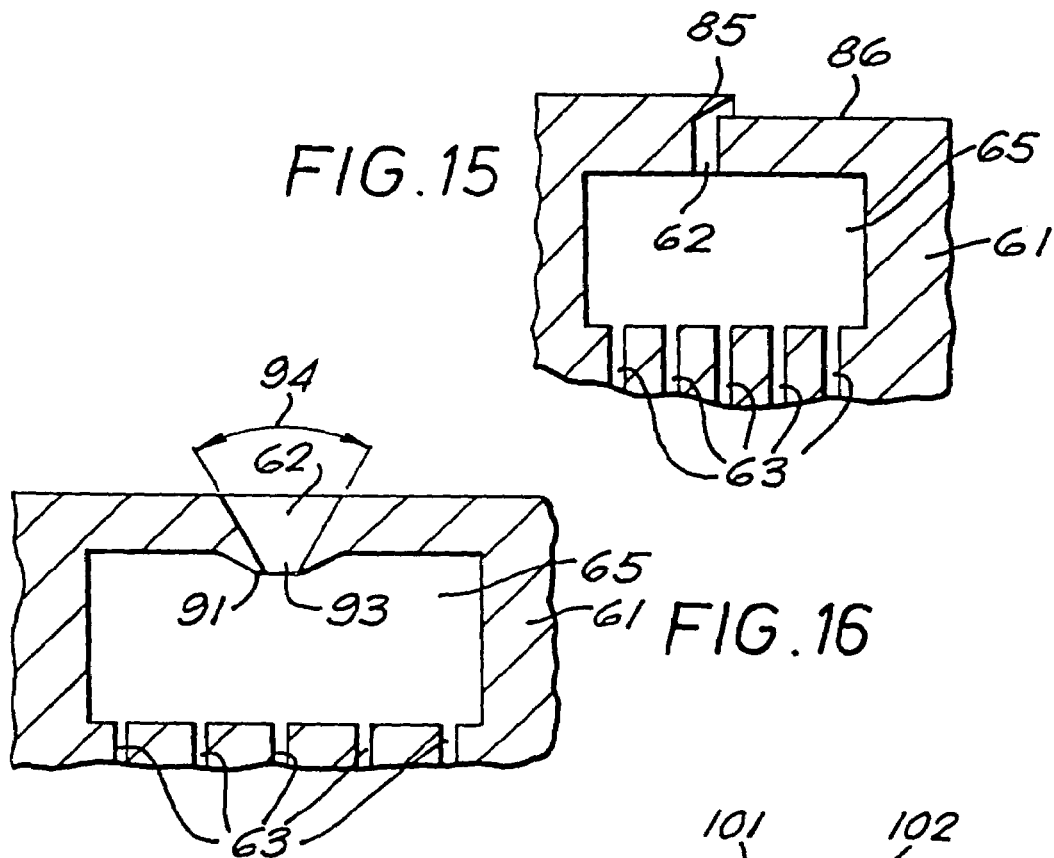
FIG. 15
FIG. 16
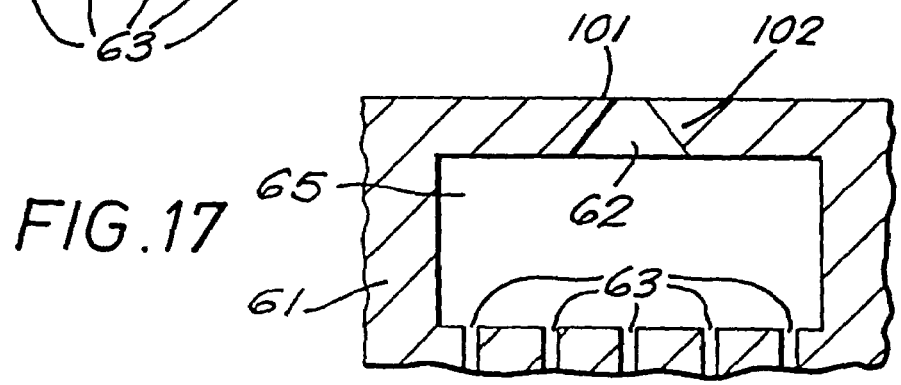
FIG. 17

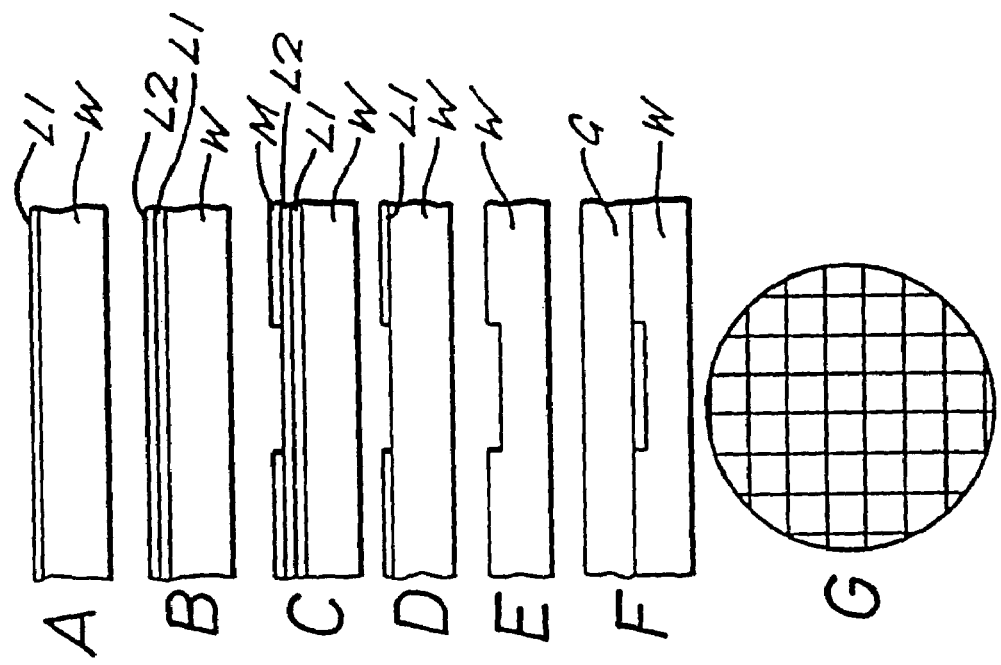
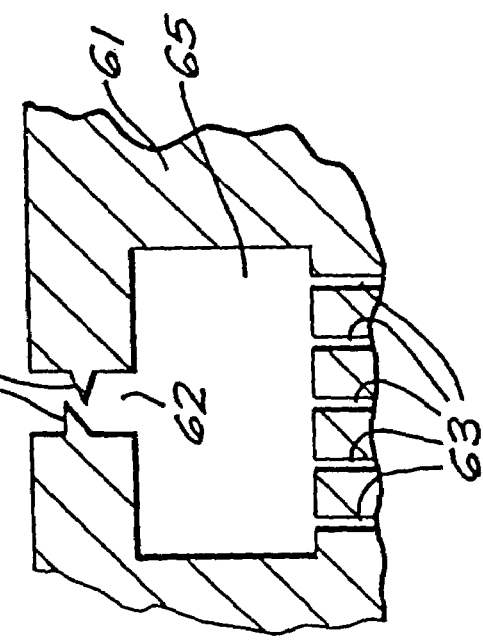
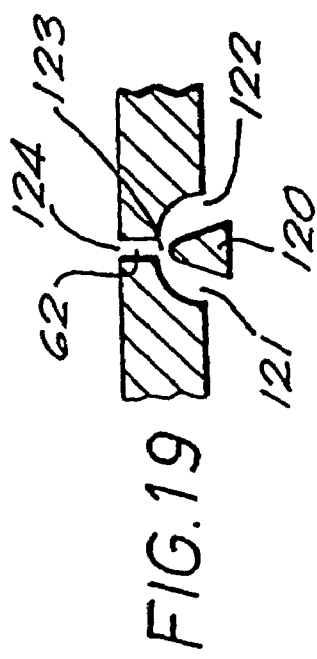

PRIOR ART

ATOMISING NOZZLE AND FILTER AND SPRAY GENERATING DEVICE

This application is a continuation of application Ser. No. 09/472,169 filed Dec. 27, 1999 now U.S. Pat. No. 6,503,362 which is a continuation of Ser. No. 09/303,670 filed May 3, 1999 now U.S. Pat. No. 6,007,676 which is a continuation of Ser. No. 08/661,741 filed Jun. 11, 1996 now U.S. Pat. No. 5,911,851 which is a continuation of Ser. No. 08/128,021 filed Sep. 29, 1999 now U.S. Pat. No. 5,472,143.

BACKGROUND TO THE INVENTION

1. Field of the Invention

The present invention relates to an atomising nozzle and to such a nozzle with a filter, notably to one which produces a spray of fine droplets suitable, for example, for the administration of a medicament by inhalation, to the production of such nozzles, and to a spray generating device incorporating such nozzles.

2. Description of the Prior Art

It is known (e.g. from WO 91/14468) that fluids can be caused to form very fine droplets on being forced through narrow nozzles at high pressure. WO 91/14468 proposes to manufacture the necessary nozzles using methods such as those known in the manufacture of spinning nozzles. These nozzles are produced, for example, by boring through a thin metal plate with a tungsten-carbide needle. An important area of application for the equipment according to WO 91/14468 is the production of aerosols for inhalation therapy. Demanding requirements are imposed among other things, on the fineness of the droplets; it has been found during numerous investigations that a considerable number of droplets must have a size less than 6 µm in order that a sufficient quantity of the medicine can reach deep enough into the lungs. For safe treatment the individual pieces of equipment must each produce the same droplet spectra, since only then is it certain that the given dose of the medicine will be delivered to the lungs in the desired way.

With the mechanical production of nozzles there are sometimes disturbing deviations from nozzle to nozzle, possibly due to the walls of the nozzles being of varying degrees of roughness. It is, amongst other things, difficult to produce double nozzles, like those shown in FIG. 8 of the afore-mentioned WO 91/14468, with the necessary accuracy. In addition, it is not an easy matter to obtain nozzles of changing cross-section using known methods, possibly with a view to accelerating or slowing down the flow of fluid in the nozzle, or to provide impact elements or vortex-generating devices.

In PCT Application No GB91/00433, there have been described methods and devices for forming sprays of fine droplets from a fluid without the use of pressurised propellant gasses, notably for the formation of sprays of a fluid medicament which have a mean droplet size of less than 10 micrometers for inhalation by a user so that the droplets of medicament can penetrate into the lower lung. In PCT Application No GB91/02145, there have been described methods and devices by which the formation of such sprays can be optimised by inducing secondary flows in the stream of fluid when it passes through the nozzle aperture.

In the preferred form of such methods and devices (for example, as shown in FIG. 21), a metered dose of the fluid medicament is drawn from a reservoir 210 into a pressure chamber 204 by retracting a piston 203 in a cylinder 202 of a pump mechanism 250 against the action of a spring 206. The piston 203 or spring 206 is latched 233 or otherwise retained in the retracted, or cocked, position so that the metered dose is held at ambient pressure in the pressure chamber 204 of the pump 250 until it is discharged. When discharge is required, the piston 204 or spring 206 is released and the spring 206 drives the piston 203 forward, thus applying a rapid pressure rise to the fluid causing it to discharge through the nozzle assembly 222 and form a spray of droplets.

The very fine droplets required for the application of a medicament to the lower lung are achieved by the use of fine aperture size nozzles and high pressures, typically with nozzle apertures of less than 20 micrometers and pressures in excess of 300 bar.

The nozzle apertures required to achieve such fine droplets can be formed in a number of ways, for example by punching a hole in a metal plate and part closing up the hole to achieve a fine aperture with a rough rim which causes the secondary flows in the fluid stream as it passes through the nozzle aperture. However, the techniques used to form the nozzle aperture either require accurate machining of components on a microscopic scale, which is expensive and time consuming and does not give consistent results, leading to rejection of components during quality control assessment prior to use or to inconsistent operation of the device. Furthermore, the need to be capable of enduring the very high pressure surge, possibly as high as 600 bar, when the device is actuated requires the use of mechanically strong components. Again, this adds to the cost of the device.

In PCT Application No GB91/02147 there has been described a form of construction which incorporates an integral one way valve and filter in the nozzle assembly to prevent air being sucked into the device through the discharge nozzle when the piston is being retracted to draw the metered dose of fluid from the reservoir and to prevent blockage of the fine nozzle aperture by solid particles entrained in the fluid. In a preferred form of such a construction a cylindrical plug is a push fit in a chamber immediately upstream of the nozzle orifice to provide an annular passage between the internal wall of the chamber and the radially outward wall of the plug. This annular passage has a radial dimension equal to or less than the nozzle aperture and thus provides a fine filter to remove solid particles which might otherwise block the nozzle aperture. The fine annular passage also imposes a flow restraint on the movement of fluid which is overcome by the high pressure generated when the piston is driven on its forward, or discharge, stroke to allow fluid to flow outwardly through the nozzle aperture. The flow restriction, however, prevents fluid from flowing back into the device as the piston is retracted. This reduces the risk of contamination of the fresh fluid drawn into the pressure chamber from the reservoir with air or fluid from the nozzle assembly downstream of the plug. Again, such a device must be manufactured from metal to be able to withstand the pressure surge as the device is operated and thus requires high precision machining of components which is expensive.

SUMMARY OF THE INVENTION

An object of the invention, therefore, is to provide a device and a method for the manufacture of a nozzle which reduces the above problems and is capable of being made with a high degree of accuracy at low cost.

In accordance with one aspect of the invention, there is provided a nozzle with one or more nozzle outlets for the atomisation of fluids, consisting of at least two plates which are connected together, possibly by an intermediate layer, wherein at least a base plate has a grooved structure which connects the intake side of the nozzle to the nozzle outlet(s).

An embodiment of the invention can thus provide a nozzle (also referred to herein as a nozzle assembly) which is composed of two or more plates; at least one of which, a base plate, is formed with grooves which join an intake side and atomiser nozzle outlets provided on an oppositely disposed side, whilst another plate (the cover plate), which will normally be unstructured, is placed upon the structured side of the base plate and is joined firmly thereto. A nozzle assembly consisting of three layers can consist, for example, of a structured silicon plate, a flat silicon cover plate and a thin glass plate therebetween. Of course the functions of the base and cover plates can be reversed with a structured cover plate overlying an unstructured base plate.

The cavities in the nozzle assembly are usually of rectangular cross-section. However, a large number of variations is possible if the nozzle assembly is manufactured by way of the method described hereinbelow and related methods known to those skilled in the art. By using different etching methods, it is also possible to produce base plates with grooves of other cross-sections if so desired.

If the cover plate is structured in addition to the base plate, then it is possible to obtain other cross-sections, e.g. cross-sections of approximately circular shape. When both the base plates and cover plates are structured, both plates are usually given identical structures. Other variations are possible if the base plate and cover plate are structured in different ways but adapted to cooperate with one another.

According to another aspect of the invention, there is provided a spray generating device comprising a nozzle assembly for forming the spray of droplets from a stream of fluid fed to it by a means for generating a flow of fluid, which nozzle assembly comprises:

a. a first member having formed in a first face thereof one or more fluid inlet(s) adapted to feed fluid to one or more fluid outlet(s) located at an edge of the first member, the outlet(s) being configured so that a spray of droplets is formed by the fluid outlet(s) from a stream of fluid flowing through them;
b. a second member secured upon the said first face of the first member and adapted to co-operate with the first member to provide one or more conduits each adapted to connect a said fluid inlet in fluid flow communication with a said fluid outlet, preferably the said second member co-operates with one or more channels formed in the said first face of the said first member to define the walls of one or more fluid conduits connecting said fluid inlet(s) to said fluid outlet(s); and
c. means for connecting said fluid inlet(s) to said means for generating the flow of fluid.

It is preferred that the fluid flow conduits each incorporate one or more narrow bore portions which have transverse dimensions and a transverse cross-section which is less than that of the fluid outlet(s) and which act as filters to protect the outlet(s) against blockage by solid particles in the fluid. The narrow bore portions also provide a flow restriction in the conduits which act as one way valves of the type described in PCT Application No GB 91/02147.

Preferably, the first member is a substantially planar member and the channel(s), fluid inlet(s) and fluid outlet(s) are formed in a face of said first member with the longitudinal axes of the channel(s) and of the inlet(s) substantially parallel to the plane of said face and the plane of the outlet aperture substantially normal (perpendicular) to the plane of the first member; and the said second member is a second generally planar member which is preferably of substantially the same planar shape and size as the first member.

The means for connecting the fluid conduits of said first member to the flow generating device is preferably provided by locating one or more of the fluid inlet(s) at an edge of the first or second members and providing means by which the first and/or second members can be mechanically connected to the flow generating device, for example by being a sealed push fit into the fluid outlet of the flow generating device. Alternatively, a third member can be provided which is secured to a second face of either the first or the second member and which is provided with a fluid conduit adapted to be put in fluid flow communication with the means for generating the fluid flow. For example, the third member can carry a spigot which is a push or other fit in the outlet to a pump mechanism of the type described in PCT Application No GB91/00433 and which has a bore which communicates with the fluid inlet(s) in the first member. The bore of the spigot can act as the cylinder of the pump mechanism in such a device.

A nozzle assembly in accordance with the invention can readily be formed as a laminated unitary construction from components which have had the appropriate channels, inlets and outlets pre-formed therein by laser, chemical etching, photo-resist or other surface engraving techniques well known in the micro-forming art to achieve simple but accurately reproducible components having substantially flat opposing faces. These components can be secured together by diffusion bonding, adhesion, welding, clamping or other suitable techniques for securing them together in sealing engagement, optionally with sealing rings or other sealing interfaces between the members by simple assembly techniques.

In accordance with a further aspect of the invention, there is provided a nozzle assembly comprising:

a. a first member, which is preferably substantially planar, having one or more fluid inlet(s) formed therein, one or more fluid outlet(s) formed at an edge of the said first member and preferably also one or more channels formed in a first face of said first member substantially parallel to the plane of said face, the channel(s) connecting the fluid inlet(s) with the fluid outlet(s) in fluid flow communication and preferably incorporating one or more narrow bore portions which are adapted to act as filters and one way valves;
b. a second member, which is preferably substantially planar and of substantially the same planar shape and size as the said first member, located upon said first face of said first member and co-operating with said first member to provide, and/or to define with the said channel(s) present in said first member, conduit(s) for connecting said fluid inlet(s) with said fluid outlet(s) in fluid flow communication; and
c. means for connecting the fluid inlet(s) of said first member in fluid flow communication with a means for generating the fluid flow.

Preferably, the fluid inlets, the fluid outlets and the connecting channels are formed wholly in the first face of the first member and the second member is a cover member secured over said first face to provide the wall forming the conduits. However, the second member can be provided with part or all of the connecting conduits, as when the second member is provided with the channels and the first member provides the closing wall for those channels. Similarly, the second member can be provided with part of the inlets and/or outlets formed therein. For example, the first and second members can have mirror image halves of the inlets, outlets and conduits cut in the opposed faces thereof whereby securing them together forms the desired whole inlets, outlets and conduits.

For convenience, the invention will be described hereinafter in terms of a first member which has the whole depth of the inlets, outlets and channels formed in the first face thereof and the second member has a substantially flat face which provides a wall to complete the inlets, outlets and conduits.

The fluid outlet(s) act as the spray generating means of the nozzle assembly. These can therefore be simple fine bore orifices which can have rough, polygonal or other cross-sections or edges, as described in PCT Application No GB 91/02145, to form a spray of droplets from a stream of fluid passing through the outlet aperture. Thus, the aperture can have a triangular, squared or other regular or irregular polygonal shape, preferably having a maximum to minimum aperture dimension of from 1:1 to 10:1. The lip of the aperture can be rough, as when the aperture is formed by an electro-sputter erosion technique in which material is removed from the first member by striking an arc between the member and an electrode. However, it is preferred that the aperture have a sharp lip thereto over which the fluid flow changes direction sharply to achieve the secondary flow in the mainstream of the fluid flow. Typically, the change in direction will be equivalent to at least 5%, preferably from 10 to 30%, of the total flow changing direction through 90°. Preferably, the change in direction occurs sharply, notably within an axial distance of less than five, preferably less than one, diameters of the width of the flow. Such change in direction, or secondary flow, can also be achieved by forming the aperture with an axially inwardly directed lip as opposed to an externally directed lip, for example where the aperture diverges along the line of flow and has an equilateral triangular plan shape with its apex directed against the intended line of flow of the fluid through the aperture. Alternatively, two channels can intersect within the plan area of the first member to form a turbulent flow in a single channel leading to the fluid outlet aperture located at the edge of the first member.

Alternatively, the change in direction can be caused by forming a flap or partial obstruction to the aperture whereby at least part of the flow of fluid through the aperture is subjected to a sharp change in direction by the flap or obstruction. Such a flap or obstruction acts on from 10 to 80% of the effective cross-section of the flow. Other forms of secondary flow generators are described in PCT Application No GB 91/02145 and the subject matter of that application is incorporated herein by this reference.

Where the fluid outlet is formed so as to generate the spray by means of the secondary flow caused by the shape and configuration of the outlet, we have found that satisfactory sprays can be produced with flow generating devices which generate a pressure low as 25 bar where comparatively large droplets are required, for example from 30 to 150 micrometers mass median droplet size. However, when droplets with a mass median size of less than about 20 micrometers are required, it will usually be necessary to use a flow generating device which generates a pressure of at least 50 bar, typically 100 to 400 bar.

The droplet size will also be affected by the nozzle aperture size. Thus, in general we have found that it is desirable to use apertures with maximum transverse dimensions of less than 500 micrometers, for example 50 micrometers or less. Where fine droplet sized sprays are required, the maximum transverse aperture dimension is preferably less than 30 micrometers. Such dimensions correspond to cross-sectional areas of from 5 to 2,500, eg. 10 to 500, square micrometers. Where coarse sprays are required, the aperture size can be to 100 micrometers maximum transverse dimension.

As indicated above, the desired spray can also be formed by causing two or more jets of fluid to impinge upon one another or for a single jet to impinge on a fixed impinger. In this case it is not necessary that the nozzle aperture cause any significant amount of secondary flow and a smooth lipped substantially circular, squared or rectangular aperture can be used. In order to produce an acceptable jet, it is preferred to use a flow generating device which generates a fluid pressure of from 50 to 400 bar and an aperture with a maximum transverse dimension of from 5 to 100 micrometers. Where two impinging jets are used, it is preferred that the line of flight of the jets include an angle of from 60 to 150°, preferably about 90 to 120°, at the point of impact and that the impact occur from 25 to 500, eg. from 30 to 100, micrometers from the plane of the edge of the first member at which the fluid outlets are located. Where a jet of fluid strikes a fixed impinger, it is preferred that this be located in the line of flight of the jet at a point before the jet begins to break up into separate droplets, typically less than 1000 micrometers downstream of the fluid outlet and that the surface of the impinger be angled to the line of flight of the jet so that the impinger is self cleaning and does not retain a significant amount of fluid thereon. A suitable form of such a self cleaning impinger is described in PCT Application No GB 92/0668.

Embodiments of the invention are described hereinafter in terms of the use of two fluid outlets to form twin jets of fluid which impinge upon one another to form a spray of droplets.

The fluid outlets are fed with fluid under pressure from the fluid flow generating means via the fluid inlet and the conduits formed in the first member. The fluid inlet is conveniently provided by a simple circular or other shaped chamber in the first member which is in direct fluid flow communication with the flow generating device via inlets at the edge of the first member or via a spigot or other means by which the nozzle assembly is mounted on the flow generating device. As indicated above, this spigot can form part of the pump mechanism of the flow generating device and can be carried by a third planar member which is mounted on the opposed face of the first member to that carrying the second member. However, the first member could be formed with the spigot formed integrally therewith, for example as a metal or other tubular projection from the second face of the member.

Embodiments of the invention will also be described hereinafter where a third member carries the spigot protruding therefrom.

A single fluid inlet chamber in the first member typically receives all the fluid fed to the nozzle assembly and distributes it to the fluid outlet(s). If desired, the fluid inlet chamber can be elongated in one or more directions to assist uniform flow of the fluid to the fluid outlets. For convenience, the invention will be described hereinafter in terms of a single generally circular inlet chamber.

The inlet feeds fluid via one or more conduits to the fluid outlet(s). As stated above, these conduits are formed by etching, engraving or otherwise forming suitable channels in the face of the first member, for example by inserting fine wires or ablatable material filaments into the interface between the first and second members so as to form depressions in the opposed faces of the members and then removing or burning away the wires or filaments to form the channels and outlets. The channels will typically have a generally squared cross-section since they are in general formed by the removal of material uniformly across the whole width of the channel.

As stated above, it is particularly preferred than the channels have one or more portions which are narrower than the aperture of the fluid outlet so that these portions act as filters to prevent solid particles which might block the fluid outlets from reaching the outlet in a manner similar to the fine bore passages described in PCT Application No GB 91/02147. Such a fine bore portion of the conduit preferably has cross-sectional dimensions which are from 10 to 80% of those of the fluid outlet. It is also preferred that the fine bore portion of the channel cause a pressure drop of from at least 0.5 bar in the flow of fluid through the portion of the channel so that the narrow bore portion inhibits withdrawal of fluid from the channel during retraction of any pump mechanism used to generate the flow of fluid through the nozzle assembly. Preferably, the pressure drop is the minimum required to prevent return flow of fluid and air from the nozzle to the flow generating device and yet does not deleteriously affect free flow of the pressurised fluid through the channels and the fluid outlet(s). The optimum flow restriction can readily be determined for any given case, but will usually achieve a pressure drop of from 1 to 3 bar or more.

Whilst the channels may communicate directly with a fluid outlet, it is preferred that the narrow bore portions of the channels be located between the fluid inlet and a plenum chamber which feeds fluid to the fluid outlets. Such a plenum chamber aids uniform distribution of the flow of the fluid to the outlets where more than one outlet is used, for example where two outlets are used to form two jets of fluid which impinge upon one another. The plenum chamber may also be configured so as to assist the formation of secondary flow in the fluid as it flows to the outlet(s), for example by incorporating curves or other wall configurations for causing swirling in the fluid flow.

The nozzle assembly finds use on a wide range of fluid flow generating devices, such as pressurised gas or aerosol type dispensers in which fluid is caused to flow out of a container by the expansion of a propellant gas. However, the nozzle assembly is of especial application in forming a spray from a flow of fluid generated by a manually operated pump mechanism, thus avoiding the use of a propellant gas. The pump mechanism may be of the type described in PCT Application NO GB 91/00433. The nozzle assembly is mounted by any suitable means upon the outlet from the pressure chamber of the pump, for example by a screw, bayonet, push or other fit, and receives the metered dose of the fluid when the spring or other energy source is released and the pressure within the pressure chamber rises. Other forms of fluid flow generator may also be used, provided that they can achieve the required pressure rise to discharge the fluid through the fluid outlet(s) as a spray with the desired mass median droplet size.

As indicated above, the channels, the fluid inlet, the plenum chamber and the fluid outlets are all formed in one face of the first member, although the fluid inlet can extend through the thickness of the first member to communicate with the fluid flow generating means. Such a design readily lends itself to fabrication by selectively removing the necessary material from the required areas of the surface of the first member by etching or engraving techniques which can be accurately controlled to form the very fine features required for the present invention. Such techniques are known and used in the formation of channels and nozzle outlets in the manufacture of ink jet printer heads, see for example U.S. Pat. No. 4,915,718 and European Application No 0397441, and in general comprise the application of a mask to a photo-resist or chemically etchable material; sensitizing the material and removing the material in the required areas by application of a suitable etching material. Alternatively, the channels can be formed by burning away the material using a laser or by striking an arc between the member and an electrode. Other methods for forming the features on the surface of the first member may be used, for example milling or fine engraving of silicon, ceramic or metal plates.

Such techniques can be used to remove accurately controlled amounts of material from accurately defined selective areas of the surface of the first member to form, within reason, any desired shape of channel, fluid outlet or other feature. Such techniques are especially applicable to planar surfaces and it is therefore preferred that the surface of the first member in which the features are to be formed is substantially flat. However, they may also be applied to curved or irregular surfaces so that the surface of the first member need not be flat if desired.

The components of the nozzle assembly for use in the present invention thus readily lend themselves to manufacture by such techniques from a wide range of materials which are conventionally used in such techniques, for example photo-resist plastic, silicon, ceramics, metals. Such materials can be produced to a high degree of accuracy and are often strong enough to resist the stresses due to the high pressure rises imposed upon the nozzle assemblies without the need for supporting framework or other structures. Furthermore, being substantially flat members, the first, second and third members can readily be secured to one another in sealing engagement. Thus, metal, silicon or ceramic plates can readily be bonded together by pressure welding or by diffusion bonding in which an interface of a suitable metal, for example gold, is located between the opposed faces of the member and bonding caused by the application of heat and pressure. Such diffusion bonding has the advantage that little distortion of the shape of the channels and other features in the face of the first member is caused, thus preserving the accuracy of the features once formed.

Alternatively, the first and second members of the nozzle assembly can be secured in position by the use of adhesives, conventional ultra-sonic or other welding techniques or by mechanically clamping the components together. If desired, sealing rings or gaskets can be located between the opposing faces to ensure a fluid tight seal. However, where the faces of the members are sufficiently flat, this will usually not be necessary and the adhesive or metal diffusion interface between the opposed faces will ensure an adequate seal.

If desired, the assembled nozzle assembly can be located within a supporting housing or the like to impart the necessary strength to the assembly to withstand the high pressures generated by the devices of our PCT Application NO GB91/00433.

In particular, the nozzle assemblies according to the invention are preferably manufactured by means of the following steps:

structuring a batch of base plates with grooves;

joining the base plates and cover plates; and separating the individual nozzle assemblies.

The grooved finish is preferably produced simultaneously for a plurality of nozzle assemblies over a large surface area in a parallel manufacturing process, and then the base and cover plates are joined in one step (i.e. a batch process).

Thereafter, the composite structure is divided into individual tiles or chips, and the inlet and outlet openings of the nozzle assemblies are opened up.

There are special advantages with this type of manufacture. The batch manufacture first of all makes it possible to produce individual component parts which are particularly cheap, and which could only be produced using serial processing methods at considerably greater expense. The batch manufacture secondly guarantees a specific constant quality for all parts which can be reproduced repeatedly under the same processing conditions, a quality which is never subject to gradual change, as would be the case in serial processing methods due to wear of the worktool(s).

Also, the position and placement of the parts in the process are determined likewise by the overall design, and does not therefore have to be altered by time-consuming sorting- or handling machines.

Thus, the present invention relates to new, highly effective nozzle assemblies and methods which can be used to produce large numbers of these nozzle assemblies so that they are of constant high quality; in addition, a filter—possibly a multi-staged filter—can be integrated in the nozzle assembly.

The materials and methods which can be used according to the invention produce nozzles which excel through a number of advantages:
high mechanical stability;
a high degree of resistance to chemical influences (e.g. aqueous medicine solutions, acids);
low surface roughness of the grooves;
low influence of larger pressure- and temperature differences;
valve function of the nozzle members filled with fluid with lower pressures.

The nozzle assemblies according to the invention can be very small in size, so that the dead volume is very small, and therefore when the nozzle members are used in the therapeutic domain (production of inhalation aerosols) the dead volume accounts for only a small fraction of the quantity of fluid to be diffused.

Surprisingly, the provision of shallow grooves means that no problems result with transportation of the fluid, despite the fact that small flow cross-sections are likely to give problems with the boundary layers.

The nozzle assembly of the invention thus offers a simplified design which does not required expensive and time consuming machining of components and which enables components to be made reproducibly to a high degree of accuracy and which can readily be assembled to form the nozzle assembly.

The invention also provides a method for producing a nozzle assembly for use in a spray generating device of the invention, wherein the fluid outlet(s), the fluid inlet(s) and the connecting channels are formed in the face of the first member by selectively removing material from that face; and securing a second member upon the said first member whereby the face of said second member opposed to said first member co-operates with the said fluid outlet(s), fluid inlet(s) and said channels to form the fluid flow paths for said nozzle assembly.

DESCRIPTION OF THE DRAWINGS

The invention will be described in more detail hereinafter, by way of example only, in terms of a number of exemplary embodiments with reference to the accompanying drawings, in which:

FIG. 1 is a schematic perspective view of a preferred embodiment of a nozzle assembly in accordance with the invention and FIG. 1A is a detail of a possible variant of a nozzle outlet for the assembly of FIG. 1;

FIG. 2 is a schematic plan view of part of a second preferred embodiment of a nozzle assembly in accordance with the invention, FIGS. 2A and 2B relating to details thereof;

FIG. 3 is a schematic plan view of part of a third preferred embodiment of a nozzle assembly in accordance with the invention employing twin nozzle outlets, FIGS. 3A and 3B relating to details of that nozzle assembly;

FIGS. 4, 4A, FIGS. 5, 5A, FIGS. 6, 6A and FIGS. 7, 7A relate to specific examples of twin nozzle outlets for a nozzle assembly in accordance with the invention;

FIG. 8 relates to a detail of a nozzle assembly comprising a plurality of nozzle outlets;

FIG. 9 relates to a detail of a nozzle assembly employing a nozzle outlet with an impinging element;

FIG. 10 and FIGS. 11A, 11B, and 11C relate to alternative designs for a nozzle outlet for use in a nozzle assembly in accordance with the invention;

FIG. 12 is a schematic plan view of part of a nozzle assembly in accordance with a further embodiment of the invention;

FIG. 13 is a schematic plan view of yet a further alternative embodiment of a nozzle assembly in accordance with the invention;

FIGS. 14,15, 16, 17, 18 and 19 relate to yet further examples of nozzle outlet designs for a nozzle assembly in accordance with the invention;

FIG. 20 represents various stages in the manufacture of a nozzle assembly in accordance with the invention; and FIG. 21 is a sectional view of a spray generating device.

DESCRIPTION OF THE PREFERRED EMBODIMENTS

FIG. 1 is a schematic exploded perspective view from above of an example of a nozzle assembly 10, or of part thereof, in accordance with the invention.

FIG. 1 shows a base plate 11 and a cover plate 12, which has been lifted off the base plate 11 for illustrative purposes. In use, with the cover mounted on the base plate 11, fluid is passed under pressure through a filter 13 at an intake side 16 of the nozzle assembly 10, which filter is composed of a number of mutually parallel narrow grooves 17, the cross-section of each groove 17 of which should be less than the cross-section of a nozzle outlet 14. From the filter 13, the fluid passes under pressure into the channels 15, from where it is expelled through the nozzle outlet 14.

FIG. 1*a* shows a variant of the grooved plate 11, in which the nozzle 14' is bent, and instead of two channels 15 which extend at an obtuse angle relative to each other as in FIG. 1, a series of parallel channels 15' is provided.

FIG. 2 shows another version of a nozzle assembly 20 in accordance with the invention. This drawing shows a view from above onto a grooved plate 21, where—as seen from the intake side 26—a coarser filter 23 with grooves 27 is followed by a finer filter 28, which is shown in a cut-out sectional drawing on a larger scale in FIG. 2*a*. The filter 28 communicates with the nozzle outlet 24 via channels 25. The right angles disposed between the channels support the cover plate (not shown) and reinforce its connection to the grooved plate 21.

It has been found that in the case of individual nozzle outlets like those in FIGS. 1 and 2, more favorable droplet spectra can be produced if the nozzles 14 and 24 are short in the flow direction. If twin nozzle outlets (see for example FIG. 3) are provided, longer (e.g. conical or tapering) nozzles can give good atomization results because the fluid jets are split into the finest droplets when they collide.

FIG. 3 shows part of a nozzle assembly 36 in which the two-stage filter 37, 38 and the five parallel channels 35 generally correspond to the filter 27, 28 and channels 25 of the embodiment shown in FIGS. 2/2a. The nozzle outlet 24 according to FIG. 2 is, however, replaced here by the twin nozzle outlet 39a/39b. As can be seen from the enlarged drawing in FIG. 3b, the twin nozzle outlets 39a/39b direct two jets at an angle of 90° relative to each other. Due to the collision of the jets, particularly good atomization is obtained. The twin nozzle outlets can be modified in various ways. Thus, both jets can, if so desired, be oriented towards each other at a more acute angle or at a more obtuse angle (about 20° to 160°, preferably 60° to 150° and more preferably 90° to 120°). In addition the cross-section of the nozzle outlets can be selected differently; for example the strong tapering of the outlets 39a/39b in FIGS. 3, 3a, may be dispensed with. As illustrated in FIG. 3b, it is desirable for the jets to impinge a slight distance away from the nozzle outlets. Smaller orientation deviations do not then result in incomplete collision of the jets on one another. The edges of the structure may be bevelled where long term use of the channel plate might cause breakages to the edges which could cause the filter or nozzle to become blocked.

FIGS. 4, 5, 6 and 7 represent plan views of alternative configurations of a twin nozzle outlet. Each of these Figures shows the nozzle outlet region only of one plate of a nozzle assembly. For illustrative purposes, a filter arrangement and the channels for the passage of fluid from the filter arrangement are not shown in FIGS. 4 to 7. The filter arrangement and channels may be configured either as shown in FIG. 1, or in FIGS. 2/3, or another suitable manner. The shaded areas represented raised portions of the grooved plate 21 with the portions not shaded representing the grooved or recessed areas.

FIGS. 4A, 5A, 6A and 7A represent enlarged views of the nozzle outlet area of the grooved plates 314, 315, 316 and 317 shown, respectively, in FIGS. 4, 5, 6 and 7. The dimensions shown in FIGS. 4/4A, 5/5A, 6/6A and 7/7A are in millimeters. The depth of the grooved (i.e. non-cross hatched) portions is 0.005 mm below that of the hatched areas in those drawings.

Figure 4:
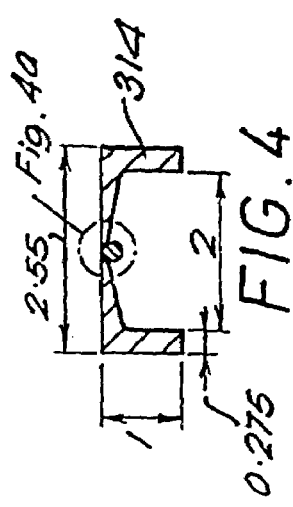
Figure 4A:
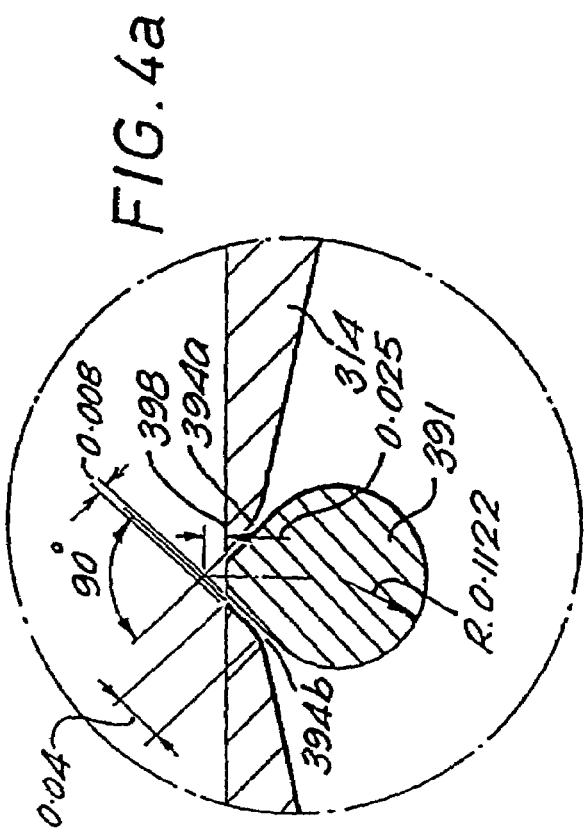

In FIG. 4A, each nozzle outlet portion 394a/394b has a length of 0.04 mm and a constant breadth of 0.008 mm. As stated before, the depth of the nozzle outlet is 0.005 mm. The central island 391 has a radius of 0.1122 mm. The nozzle outlets are arranged so that the fluid jets exit the nozzle outlets at 90° with respect to each other and collide at 0.025 mm from the outlet surface 398 of the nozzle assembly.

Figure 5:
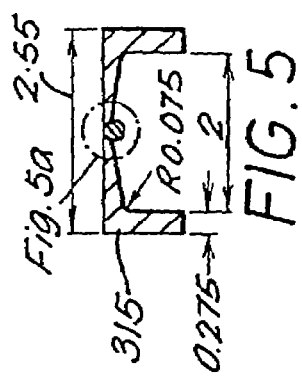
Figure 5A:
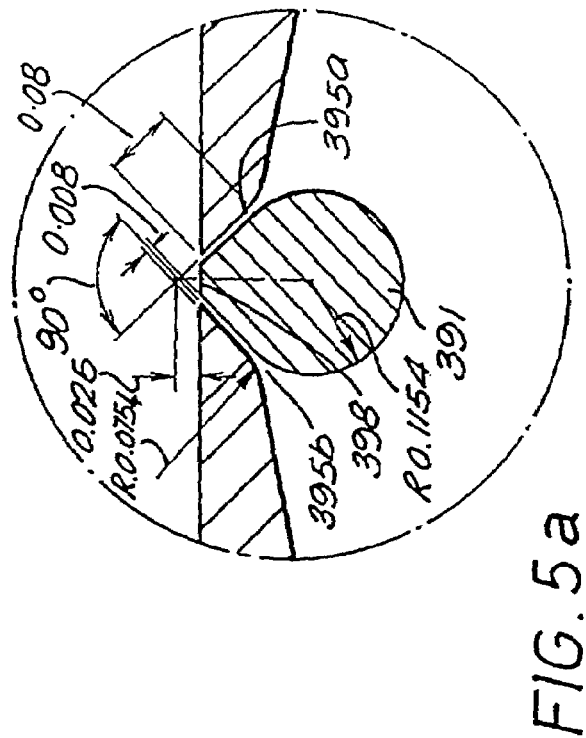

In FIG. 5A, the outlet nozzles are shown to have a length of 0.08 mm with a constant (nozzle outlet portion 395a/395b) width of 0.008 mm, and a depth, as before, of 0.005 mm. The nozzle outlets are configured so that the fluid jets exit at 90° with respect to each other and collide at a distance of 0.0025 mm from the outlet surface 398 of the nozzle assembly.

In FIG. 6A, the nozzles have the same configuration as in FIG. 5A with nozzle outlet portions 396a/396b. However, in FIG. 6A, the island portion 392 is configured differently from the island portion 391. It will be seen that the inner surface of the island portion 391 and also the inner surface of the outer wall regions 393 are configured to have a concave radius of curvature of 0.2 mm.

In the arrangement shown in FIG. 7A, the outer wall and island portions are configured similarly to those in FIG. 6A. Also, the overall nozzle outlet configuration is similar to that in FIG. 6A, with the exception that the nozzle outlets are arranged to be slightly tapered, having a width of 0.007 mm at the inner end and a width of 0.008 mm at the outer end. This configuration is intended to facilitate the removal of particles through the nozzle should such particles pass the filters shown in FIGS. 2/3 and reach and enter the nozzle outlet portions 397a/397b.

Figure 8:
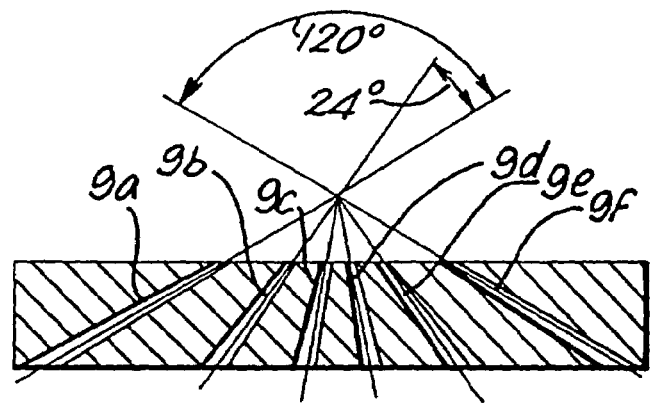
Figure 9:
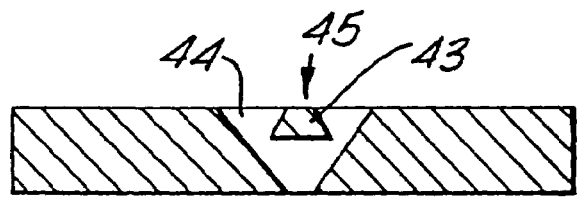
Figure 10:
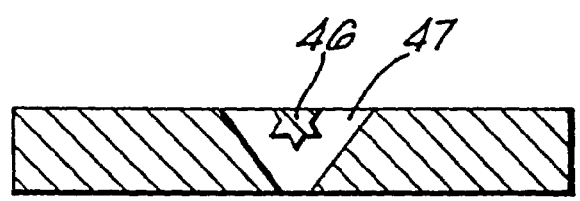
Figure 11A:
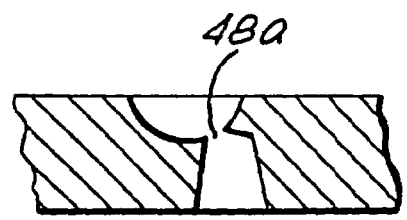
Figure 11B:
Figure 11C:
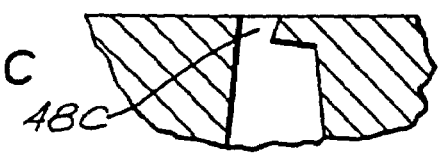

FIG. 8 shows the nozzle outlet region of a nozzle assembly according to the invention wherein six nozzle outlets 9a to 9f are oriented in such a way that the jets which issue therefrom meet at a point. This can avoid a situation where the other jets no longer collide if one of the nozzles becomes blocked. In FIG. 9, an impact element 43 is provided in the mouth 44 of a nozzle outlet 45, which widens towards the outside. Similarly, in FIG. 10, a vortex-generating structure 46 is fitted into a mouth 47 of the nozzle outlet which promotes a greater vortex formation of the issuing fluid. FIGS. 11a to 11c also show a section of the nozzle assembly in the region of the nozzle outlet, wherein various geometric shapes for the nozzle outlets are illustrated at 48a, 48b and 48c.

To improve the atomization, the nozzle outlet can also be designed in such a way that it is somewhat longer and is provided with a region of reduced thickness, into which region an air channel or air channels open so that—as with a water-jet pump—air is carried into the jet of fluid.

It has been found that a favourable droplet, or particle size, is typically obtained if the narrowest cross-sectional surface area of the nozzle outlet, or outlets, is between about 25 and 500 $\mu m^2$. When the grooves in the base plate are, for example, 5 $\mu m$ in depth, it is possible for the nozzles to be kept to a comparable width and typically their width-/breadth ratio is between about 1:1 and 1:20. Relationships outside these regions are also possible. The skilled person can, if necessary, optimize the appropriate nozzle outlet dimensions by carrying out tests as the characteristics of the fluid to be sprayed, as the surface tension and the viscosity are also relevant to a certain degree. The specific characteristics of the fluid to be sprayed need to be considered in particular when that fluid includes an organic solvent or an oil rather than a watery fluid, of the type for which the present device is primarily, but not exclusively, intended.

To exclude the possibility of blockage of the filters, even over long-term use, the filter can also be designed so that it is of zig-zag, meander-like or arcuate configuration. Thus, a greater number of through passages (of constant size) is formed. In addition, if so desired, instead of a one-or two-staged filter it is possible for three-staged filters to be provided with respectively narrower through passages. In each case, however, it must be ensured that a sufficiently high pressure is available at the nozzle despite the reduction of pressure in the filter system.

The cross-sectional shape of the nozzle outlet or the sum of the cross-sections of the nozzle outlet can be varied within further boundaries. At a given pressure, the cross-section of a slitted nozzle outlet can be considerably greater than the cross-section of a square or round nozzle outlet, without the droplet spectra being impaired. The cross-section of the nozzle outlets or the sum of the cross-sections is usually between 5 and 2000 $\mu m^2$, preferably between 20 and 1000 $\mu m^2$ and in particular between 25 and 500 $\mu m^2$. This also applies when two or more parallely orientated nozzle outlets are provided.

When, also, in particular in the case of very narrow or very flat nozzle openings, surface edge effects play a large role, the skilled person needs to take account of the knowledge of the physics concerning hydraulic cross-section in the determination of the arrangement of the nozzle outlets and the choice of the dimensions therefor.

Figure 12:
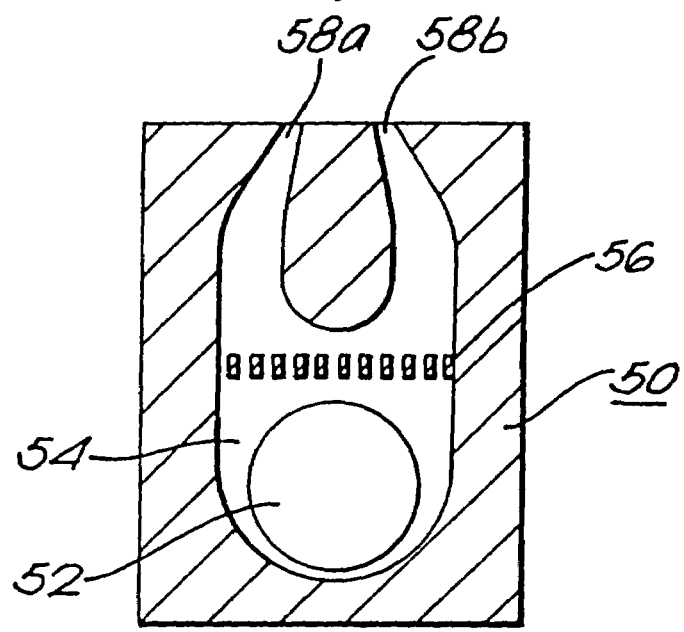

FIG. 12 is a schematic representation of part of another nozzle assembly in accordance with the invention. FIG. 12 represents a plan view of a base plate 50 in which channels are formed. An inlet 52, which extends perpendicularly to the plane of the base plate 50, opens into a chamber 54. The chamber is connected via one or more filter stages 56 to twin nozzle outlets 58a and 58b. The provisional of the perpendicularly extending inlet enables a compact construction of the nozzle and/or nozzle assembly.

Figure 13:
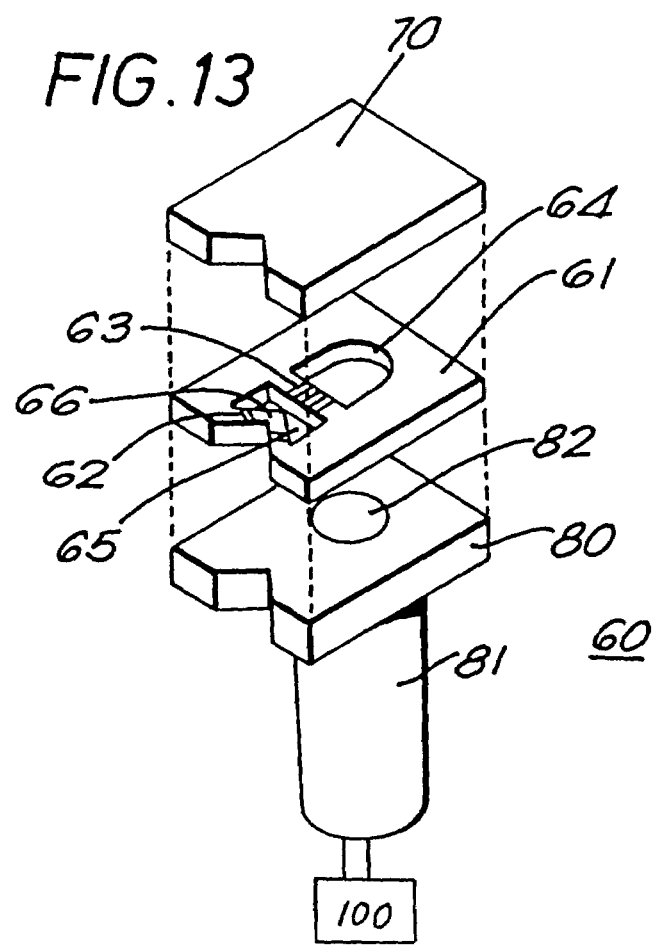
Figure 21:
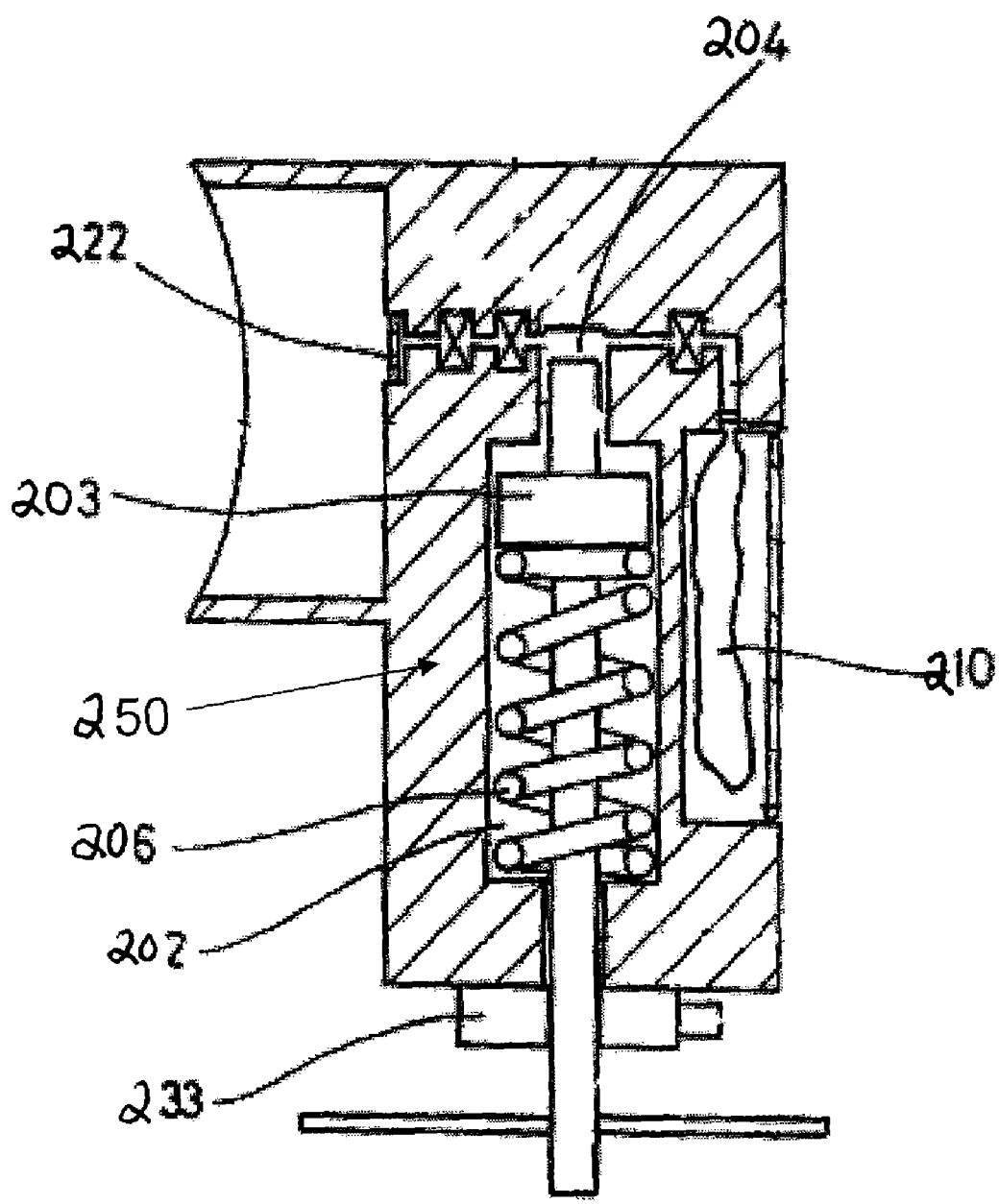

FIG. 13 shows an example of nozzle assembly 60 with an inlet disposed perpendicularly to the connecting surfaces as in FIG. 12.

In the nozzle assembly of FIG. 13, a first plate member 61 has a first set of two channels 62 in its upper face which debouch at one edge of the plate. The resultant apertures at the plate edge form two fluid outlets which, in the present example, will form two impinging jets of fluid angled at about 100 to 120° to one another when fed with fluid. Preferably, the edge of plate 61 is indented at this point to provide a recess in the face of the nozzle assembly within which the two jets of fluid can impinge and form the spray of droplets. The lips of the mouths of the channels 62 where they intersect the edge of the plate 61 are sharply formed and not rounded. The face of plate 61 also carries a second set of channels 63, which are of smaller cross-section dimensions than the first channels 62. These act as the narrow bore portions linking a fluid inlet 64 cut through plate 61 with the first set of channels 62 and serve to filter out solid particles which might otherwise block the first channels and the fluid outlets. Typically, the second channels 63 each have a cross-sectional area which is approximately 10% or less of the cross-sectional area of each of the first channels 62, so as to give a pressure drop of about 10% of the applied pressure from the flow generating device, for example of from 0.2 to 25 bar, across the second channels. Typically, the second channels 63 will have at least one cross-sectional dimension which is about 50% of the corresponding dimension of the first channels. Since the channels are typically formed by removing a uniform depth of material from the surface of the first plate member, the channels will usually have a constant depth and variations in the dimensions or area of the channels is achieved by varying the width of the channels.

The second set of channels 63 debouch into a plenum chamber 65 cut into the top face of plate 61. If desired, the chamber 65 can be cut through the thickness of plate 61, but it is preferred to form chamber 65 within the thickness of plate 61 as shown. Chamber 65 is preferably configured so that the first channels 62 exit from opposed corners of the chamber 65 and a septum 66 of the material of the surface of plate 61 can be retained between the channels 62 to aid changes in direction of flow of fluid within chamber 65 and to direct the flow into the first channels 62.

A second plate member 70 is shown overlying but detached from the first plate member 61. When this second plate 70 is secured to the top face of plate 61 it provides the top faces to the channels 62 and 63 so that they form two groups of conduits which form the nozzle outlets 62 and the filter bores 63.

A third plate member 80 is also shown detached and underlying plate 61. Plate 80 carries a fluid inlet spigot 81 by which the nozzle assembly can be mounted on the outlet of a pump or other fluid flow generating device 100. The spigot 81 has an internal bore 82 which is in register with the inlet 64 in plate 61 and can form part of the pump mechanism of the flow generating device as indicated above. The exterior of spigot 81 can carry screw thread or other means (not shown) by which the spigot is secured to the pump or other flow generating means 100.

The plates 61, 70 and 80 can be formed from any suitable material, for example a photo-resist glass, ceramic or plastic or a metal, and the features in plate 61 formed by removing material from plate 61 in the desired locations by a conventional chemical etching process. Alternatively, the features can be formed by removal of material using a laser. Since the features are formed on the exterior of a substantially flat member, there is no need for complex machining of components or assembly of sub-components.

The plate members present opposed substantially flat faces to one another and can readily be bonded or otherwise secured to one another using any suitable technique, for example by ultra-sonic welding, by adhesion or by clamping them together using a metal surround which is crimped into position.

In operation, fluid at pressure is delivered to the bore 82 of spigot 81, from which is flows through inlet chamber 64 in plate 61, through the filter channels 63 to the plenum chamber 65 and thence to the nozzle channels 62. The fluid exits from the two nozzle channels as jets of fluid which impinge on one another to form a spray of fine droplets.

By applying the fluid at a pressure of at least 40 bar to nozzle channels having a mean diameter of about 10 micrometers, droplets with a mean droplet size of less than 10 micrometers were produced.

The nozzle assembly could be manufactured repeatedly to close tolerances and samples of the nozzle assembly repeatedly performed to give the same droplets sized spray.

Accordingly, from a further aspect, the present invention provides a nozzle and filter assembly characterised in that it comprises:

a. a first plate into which are formed: 1: a first group of channels having one end thereof located at the plate boundary; and 2: a second group of channels of equal or smaller size than said first group; and b. a second plate that sealingly engages said first plate so the surface of said second plate co-operates with the first group of channels in said first plate to form a first series of fluid outlets and with said second group of channels in said first plate to form a second set of fluid conduits having a cross-sectional size equal to or smaller than the said fluid outlets, whereby when a fluid is passed through said second group of channels they act as a filter to protect the first set of channels which act as spray forming fluid outlets; and c. means of connecting said two sets of channels.

Preferably the nozzle assembly is connected to means for supplying first set of channels with fluid.

In the alternative forms of plate 61 shown in FIGS. 14 to 19, the outlet to the channels 62 is modified so that the fluid issues from the outlets as a spray without the need for impingement of two jets of fluid. Thus, in FIG. 14 the outlet 74 to channel 62 is formed as a tortuous bend to induce secondary flow as the fluid exits the channel 62. To achieve a spray of droplets with a mass median droplet size of about 5 micrometers, the fluid outlet by channel 62 is from 2 to 15, preferably from 3 to 8, micrometers square in cross-section.

In the alternative form shown in FIG. 15, a flap 85 is formed at the mouth of channel 62 and the edge of plate 61 is cut away in the area 86 downstream side of the flap.

In the alternative shown in FIG. 16, the channel 62 is formed with a knife edge entry 91 having a gap 93 of from 4 to 30 micrometers and channel 62 diverges from that knife edge entry at an included angle 94 of from 60 to 150°, preferably from 90 to 120°. In the modification shown in FIG. 17, the knife edge 101 is formed at the exit to channel 62 at the edge of plate 61 and sufficient wall thickness 102 is retained between the edge of the plate and the plenum chamber 65 to ensure the rigidity and strength of the knife edge.

In the alternative shown in FIG. 18, the side walls of channel 2 are radially indented to provide a series of projections 111, 112, into the flow of fluid through the channel which induce secondary flow in the fluid as it passes through the mouth of the channel. Typically, with a channel having a maximum mouth cross-sectional dimension of from 5 to 20 micrometers, the projections 111 and 112 will be from 3 to 8 micrometers.

In the modification of the device of FIG. 13 shown in FIG. 19, a septum 120 is formed within the plenum chamber which is separated from the wall of the chamber to provide two passages 121 and 122 which form two impinging flows of fluid in a swirl chamber 123 which debouches into a single outlet channel 62 to provide the secondary flow to form a spray as the fluid exits the mouth 124 of channel 62.

As indicated above, the depth and width of the channels formed in the first plate depend on the application of the nozzle assembly. For instance, when the nozzle assembly is used to spray hair sprays, the total cross-sectional area of the fluid outlet channels is typically 1500 square micrometers. If a single channel is used, this will be typically 40 microns deep by 40 microns wide. To achieve the required particle size of typically 40 micron mass mean diameter using such a nozzle assembly, fluid at a pressure of between 30 and 150 bars is used.

If the nozzle assembly is used to spray lung deposited drugs for administration by inhalation, then typically the total cross sectional area of the outlet channel (e.g. 62) will be between 30 and 200 square micrometers. If a single outlet channel (e.g. 62) is used, this will typically be 10 microns deep by 10 microns wide. The operating pressure required to achieve a spray with a mass median droplet size of less than 6 micrometers will be between 100 and 400 bars.

The nozzle assembly of the invention may be used in other applications where a simple, rugged device is required, for example in fuel injection systems for internal combustion engines, where a group of spray nozzles would typically be used either formed in one plate assembly or using a number of plate assemblies.

A method of manufacture of a nozzle assembly in accordance with an embodiment of the invention comprising a grooved base plate and an unstructured cover plate will now be described. It will be appreciated that the method to be described can readily be modified for producing nozzle assemblies where the cover plate is structured instead of or in addition to the base plate and/or where an intermediate plate is structured.

In particular, in the method to be described, the nozzle assemblies are manufactured using the following steps:

structuring a batch of base plates with grooves;

joining the batch of base and cover plates together; and separating the individual nozzle assemblies.

The base plate is preferably structured in per se known manner using a light optical lithographic technique in conjunction with an ion-supplemented reactive dry etching technique. The heights of the structures are between 2 and 40 μm, usually between about 3 and 20 μm, preferably between about 4 and 14 μm and particularly between 5 and 7 μm. The material used for the base plate is preferably a mono-crystalline silicon since this is cheap and available in a condition (i.e. in wafers) in which it is sufficiently flat and parallel and of low surface roughness, and it can be joined to the cover plate without the additional application of adhesives or other materials during the subsequent joining process. In order to produce a plurality of nozzle assemblies in parallel, a plurality of structure base plates are formed on a wafer of silicon.

It will be appreciated that materials other than silicon can undergo structuring, and these can also be firmly joined to the cover plate in the subsequent joining process. Such materials are gallium-arsenide or metals such as aluminium or nickel-cobalt-alloys, for example, which can likewise be joined properly to a glass plate.

A thin layer of silicon is thermally oxidised on the surface of the wafer W (FIG. 20A) to be structured. The oxide layer later acts as a mask when the groove finish is etched. A light-sensitive plastics layer L2 is then applied over the layer L1 in a centrifuging process, and allowed to solidify (FIG. 20B). The groove structures are then transferred to and developed in the plastics layer using optical light by contact copy with a mask M, to a scale of 1:1 (FIG. 20C). In the next step of the procedure, the plastics structures act as masks for structuring the silicon oxide layer. The structuring is effected by reactive etching with ion beams. During the structuring of the oxide layer, the plastics material is completely removed (FIG. 20D).

The oxide layer structured in this way then acts as a mask for etching the grooves, which may be 5-7 μm in depth, in the silicon. When this is done, the oxide layer is also slowly removed (FIG. 20E).

At the end of the structuring process, U-shaped or rectangular box-shaped grooves are formed on the silicon plate, but these grooves can be of any geometric surface shape in the plan view.

With structuring of the base plate, other etching methods can be used to achieve a number of variants to give other shapes of groove which result in end products with nozzles of varying opening cross-section. Thus, for example, trapezoidal grooves can be produced by over-etching or under-etching in the appropriate way. These etched forms can be produced both by isotropic dry etching methods and by isotropic wet etching methods. If anisotropically acting etching methods (both with reactive ion plasma and also with wet chemical media) are used it is possible to produce nozzles of triangular cross-section from V-shaped grooves in mono-crystalline base plates. The geometric shape of the grooves can also be altered by combining etching techniques with coating techniques. Virtually any geometric shape can be produced.

After structuring, the silicon plate is cleaned and the rest of the silicon dioxide is removed by the wet-chemical method. The silicon plate is then joined (FIG. 20F) to a glass plate G by anodic bonding (cf. U.S. Pat. No. 3,397,278 of 13.8.1968, Pomerantz, D.I. et al.)

An alkali borosilicate glass such as Pyrex, for example, (#7740 Corning) or Tempax (Schott) is suitable for anodic bonding of silicon and glass. The glass plate is placed on the structured silicon plate and is contacted with an electrode. The entire composite structure is heated to temperatures of between 200 and 500° C. (preferably to about 450° C., because up to this temperature the thermal expansion coefficients are still close to one another and at the same time the alkali ions are sufficiently mobile for a fast bonding process) and a negative voltage of about 1000 V is placed between the silicon plate and the glass plate. Due to this voltage, the positively charged alkali ions move through the glass to the cathode, where they are neutralised. At the point of transition between the glass and the silicon, a negative spacial charge is formed in the glass which causes electrostatic drawing together of the two surfaces, and also results in a durable chemical bonding being formed between the glass surface and the silicon surface by means of oxygen bridging bonds.

In this connection, it is also particularly advantageous to use glass as the cover material for reasons of quality control, since it is easily possible to visually detect the efficiency of the bonded connection and also defects or foreign particles which lead to malfunctions of the component part.

However, other cover materials other than glass can be used. With high temperature loads it is possible to optimise the thermal expansion coefficients of the composite member if silicon is used both for the base plate and for the cover plate. For the joining process, a thin glass layer is applied to the two plates, e.g. in an evaporating- or sputtering method, by means of which the bonding process can then be carried out. In this case, a visual inspection can be made using infra-red viewing apparatus.

After the bonding process, the composite structure (see FIG. 20G) is divided into individual units (e.g. squares) by a fast rotating diamond circular saw, wherein the intake openings and the outlet openings are opened up. If the cross-sectional surface area is very different at the outlet (as with nozzle-shaped outlet openings, for example), then the separating cut must be positioned with precision to a few micrometers in order to obtain a defined nozzle outlet. Such positioning also minimises the expanse of the outward flow at the outlet.

During the separation stage, particularly high revolutionary speeds are needed (usually more than 30000 revs/min) in order to avoid expulsion at the side walls and edges of the nozzle member. Such expulsion could cause undesirable changes to the cross-section to the geometric shape of the outlet.

After dividing them up, the nozzle assemblies are cleaned and are fitted inside appropriate holders.

Although illustrative embodiments of the invention have been described in detail herein with reference to the accompanying drawings, it is to be understood that the invention is not limited to those precise embodiments, and that various changes and modifications can be effected therein by one skilled in the art without departing from the spirit and scope of the invention as defined by the appended claims.

For example, although various embodiments of the invention are described separately herein, it will be appreciated that features from the various embodiments may be combined as appropriate in yet further embodiments.

We claim:

1. A spray generating device comprising:

(a) a reservoir configured to hold a medicament;

(b) a pump, having a piston, a spring and a cylinder, wherein the piston has a retracted position and a deployed position;

(c) a pressure chamber, wherein a metered dose of the medicament is drawn from the reservoir into the pressure chamber by movement of the piston to the retracted position and held at ambient pressure in the pressure chamber until discharged, such that when discharge is required, the piston moves from the retracted position to the deployed position by virtue of the spring driving the piston forward and applying a rapid pressure rise to the metered dose of medicament to thereby cause the medicament to discharge from the spray generating device; and (d) a nozzle assembly, wherein the nozzle assembly atomizes the discharge fluid to form a spray having droplets suitable for inhalation, said nozzle assembly comprising:

(i) a first member having a first surface, the first surface having a plurality of grooves formed therein;

(ii) a second member having a second surface, requiring the first and the second surfaces to be joined together to form a plurality of passageways; and (iii) a plurality of nozzle outlets disposed at one end of the plurality of passageways, wherein the plurality of nozzle outlets are configured to discharge a plurality of fluid jets, so that the jets impinge on one another to thereby atomize the flow of fluid.

2. The spray generating device of claim 1, further comprising a filter disposed at one end of the plurality of passageways of the nozzle assembly.

3. The spray generating device of claim 1, wherein the plurality of passageways of the nozzle assembly are substantially rectangular in cross-section.

4. The spray generating device of claim 1, wherein the plurality of jets impinge at an angle of approximately 60 degrees to approximately 150 degrees.

5. The spray generating device of claim 1, wherein the plurality of jets impinge at an angle of approximately 90 degrees to approximately 120 degrees.

6. The spray generating device of claim 1, wherein the plurality of jets impinge at an angle of approximately 90 degrees.

7. The spray generating device of claim 1, further comprising a plenum chamber formed in the first member, wherein the plenum chamber is in fluid communication with the plurality of passageways.

8. The spray generating device of claim 1, wherein the plurality of passageways are substantially parallel to each other.

9. The spray generating device of claim 1, wherein the nozzle assembly further comprises a fluid inlet.

10. The spray generating device of claim 9, wherein the fluid inlet is disposed substantially at a right angle to the first member.

11. The spray generating device of claim 10, further comprising a fluid inlet chamber into which medicament is received from the fluid inlet, wherein the fluid inlet chamber is in fluid communication with the plurality of passageways.

12. The spray generating device of claim 1, wherein the plurality of passageways are configured to receive a flow of medicament supplied at a pressure of at least 50 bar.

13. The spray generating device of claim 1, wherein the plurality of passageways are configured to receive a flow of medicament supplied at a pressure of approximately 50 bar to approximately 400 bar.

14. The spray generating device of claim 1, wherein the plurality of passageways are configured to impose a pressure drop of approximately 0.2 bar to approximately 25 bar to the flow of medicament.

15. The spray generating device of claim 1, wherein the plurality of nozzle outlets have a total cross-sectional area of approximately 25 to approximately 500 square micrometers.

16. The spray generating device of claim 1, wherein the plurality of nozzle outlets have a total cross-sectional area of approximately 30 to approximately 200 square micrometers.

17. The spray generating device of claim 1, wherein the first member comprises silicon.

18. The spray generating device of claim 17, wherein the first member further comprises glass.

19. The spray generating device of claim 1, wherein the second member comprises silicon.

20. The spray generating device of claim 19, wherein the second member further comprises glass.

* * * * *

UNITED STATES PATENT AND TRADEMARK OFFICE
CERTIFICATE OF CORRECTION

PATENT NO. : 7,246,615 B2
APPLICATION NO. : 10/291624
DATED : July 24, 2007
INVENTOR(S) : Bartels et al.

Page 1 of 1

It is certified that error appears in the above-identified patent and that said Letters Patent is hereby corrected as shown below:

On the cover page, item (63) Related U.S. Application data, please replace "5,911,851, which" with --5,911,851, which is a continuation of application No. 08/462,680, filed on Jun. 5, 1995, now Pat. No. 5,547,094, which--.

In column 1, line 9, please replace "5,911,851 which" with --5,911,851, which is a continuation of application No. 08/462,680, filed on Jun. 5, 1995, now Pat. No. 5,547,094, which--.

In column 7, line 4, please replace "preferred than the" with --preferred that the--.

In column 9, line 46, please replace "does not required expensive" with --does not require expensive--.

In column 14, line 26, please replace "from which is flows" with --from which it flows--.

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 7,246,615 B2
APPLICATION NO. : 10/291624
DATED : July 24, 2007
INVENTOR(S) : Bartels et al.

Page 1 of 1

It is certified that error appears in the above-identified patent and that said Letters Patent is hereby corrected as shown below:

On the cover page, section (63) please replace "5,547,094, which is a continuation of application No. 08/128,021" with --5,547,094 which is a division of application No. 08/128,021--.

In column 1, line 9, please replace "5,547,094, which is a continuation of Ser. No. 08/128,021" with --5,547,094 which is a division of Ser. No. 08/128,021--.

Signed and Sealed this

Twenty-second Day of December, 2009

David J. Kappos
*Director of the United States Patent and Trademark Office*